United States Patent
Cox et al.

(10) Patent No.: US 10,010,534 B2
(45) Date of Patent: Jul. 3, 2018

(54) INTRAVENOUS FORMULATION AND LC/MS/MS ANALYSIS METHOD FOR GMC1

(71) Applicants: Marc Cox, El Paso, TX (US); Huan Xie, Houston, TX (US); Oscar Ekpenyong, Houston, TX (US)

(72) Inventors: Marc Cox, El Paso, TX (US); Huan Xie, Houston, TX (US); Oscar Ekpenyong, Houston, TX (US)

(73) Assignees: THE BOARD OF REGENTS OF THE UNIVERSITY OF TEXAS SYSTEM, Austin, TX (US); TEXAS SOUTHERN UNIVERSITY, Houston, TX (US)

( * ) Notice: Subject to any disclaimer, the term of this patent is extended or adjusted under 35 U.S.C. 154(b) by 0 days.

(21) Appl. No.: 15/471,102

(22) Filed: Mar. 28, 2017

(65) Prior Publication Data

US 2017/0281600 A1    Oct. 5, 2017

Related U.S. Application Data

(60) Provisional application No. 62/314,579, filed on Mar. 29, 2016.

(51) Int. Cl.
| | | |
|---|---|---|
| A61K 31/4184 | (2006.01) | |
| A61K 47/10 | (2017.01) | |
| A61K 47/14 | (2017.01) | |
| A61K 45/06 | (2006.01) | |
| A61K 9/00 | (2006.01) | |
| A61K 9/127 | (2006.01) | |
| A61K 9/08 | (2006.01) | |
| G01N 33/487 | (2006.01) | |

(52) U.S. Cl.
CPC ........ *A61K 31/4184* (2013.01); *A61K 9/0019* (2013.01); *A61K 9/08* (2013.01); *A61K 9/1271* (2013.01); *A61K 45/06* (2013.01); *A61K 47/10* (2013.01); *A61K 47/14* (2013.01); *G01N 33/487* (2013.01)

(58) Field of Classification Search
None
See application file for complete search history.

(56) References Cited

FOREIGN PATENT DOCUMENTS

WO    WO 2016029068 A1 *   2/2016   ............. A61K 45/06

OTHER PUBLICATIONS

Strickley, Solubilizing Excipients in Oral and Injectable Formulations, Pharmaceutical Research, vol. 21, No. 2, Feb. 2004.*
Cheung-Flynn et al., "Physiological role for the cochaperone FKBP52 in androgen receptor signaling." *Mol. Endocrinol.*, 19:1654-66 (2005).
De Leon et al., *Proc Natl Acad Sci USA*, 2011, 108(29):11878-834.
Estebanez-Perpina et al., *Proc. Natl. Acad. Sci. USA*, 104:16074-79 (2007).
Heinlein et al., "Androgen receptor in prostate cancer." *Endocrine Reviews*, 2004, 25(2):276-308.
Liang et al., "Quantification of a New Anti-Cancer Molecule MJC13 Using a Rapid, Sensitive, and Reliable Liquid Chromatography-Tandem Mass Spectrometry Method," *Am J Mod Chromatogr*, 2014, 1(1):1-11.
Liang et al., *Biomed Chromatogr*, 2013, 27(1):58-66.
Matuszewski et al., "Strategies for the assessment of matrix effect in quantitative bioanalytical methods based on HPLC-MS/MS." *Analytical Chemistry*, 2003, 75(13):3019-30.
Riggs et al., *EMBO J.*, 22:1158-67 (2003).
Storer Samaniego et al., *PLoS One*, 2015, 10(7):e0134015.
Tranguch et al., *J. Clin. Invest.*, 117:1824-34 (2007).

* cited by examiner

*Primary Examiner* — Svetlana M Ivanova
(74) *Attorney, Agent, or Firm* — Norton Rose Fulbright US LLP (57) ABSTRACT

Certain embodiments are directed to a GMC1 co-solvent formulation. The GMC1 co-solvent formulation described herein can be used for the treatment of prostate cancer, benign prostatic hypertrophy, and other hormone-related conditions involving androgen, glucocorticoid, and progesterone receptors.

4 Claims, 9 Drawing Sheets

INTRAVENOUS FORMULATION AND LC/MS/MS ANALYSIS METHOD FOR GMC1

PRIORITY CLAIM

This application claims priority to U.S. Application No. 62/314,579 filed Mar. 29, 2016, which is incorporated herein by reference in its entirety.

STATEMENT REGARDING FEDERALLY FUNDED RESEARCH

This invention was made with government support under grants 1SC3GM102018-01 5G12MD007605-23, 5G12RR008124, G12MD007592, and SC1GM084863 awarded by the National Institutes of Health. The government has certain rights in the invention.

BACKGROUND

Steroid hormone receptors, including androgen receptor (AR), glucocorticoid receptor (GR), and the progesterone receptor (PR), require the ordered assembly of various chaperone and co-chaperone proteins in order to reach a functional state. The final stage in the receptor maturation process requires the formation of a multimeric complex consisting of an Hsp90 dimer, p23, and one of several large immunophilins. Previous studies have demonstrated that (i) the large immunophilin, FK506-binding protein 52 (FKBP52), acts to potentiate GR, AR, and PR receptor signaling pathways, and (ii) FKBP52-mediated regulation of receptor function appears to be localized to the receptor hormone binding domain. In cellular studies, FKBP52 has been shown to preferentially regulate GR, AR, and PR receptor-mediated signal transduction (See, for example, Cheung-Flynn et al., *Mol. Endocrinol.*, 19:1654-66 (2005); Riggs et al., *EMBO J.*, 22:1158-67 (2003); Tranguch et al., *J. Clin. Invest.*, 117:1824-34 (2007)). Given its receptor specificity, FKBP52 represents an attractive therapeutic target for the treatment of hormone-dependent diseases.

To date, the only known compounds for inhibition of AR function are related to selective AR modulators that bind to the hormone binding pocket, and are therefore competitive inhibitors of endogenous hormone binding. It has been shown that when certain molecules bind to the binding function 3 (BF3) region of the AR hormone binding domain they can generally inhibit AR function in the 100 μM range. See, Estebanez-Perpina et al., *Proc. Natl. Acad. Sci. USA*, 104:16074-79 (2007). However, there still exists a need for compounds and formulations for providing selective AR modulators which are not competitive agonists or antagonists to endogenous hormone binding.

SUMMARY

GMC1 is a compound for the treatment of cancer and other androgen, glucocorticoid, and progesterone receptor related diseases or conditions. Due to its poor water solubility, it is important to develop a water-soluble and stable intravenous formulation of GMC1 for administration of the compound.

Certain embodiments are directed to a GMC1 co-solvent formulation. The GMC1 co-solvent formulation described herein can be used for the treatment of prostate cancer, benign prostatic hypertrophy, and other hormone-related conditions involving androgen, glucocorticoid, and progesterone receptors. Certain embodiments are directed to a water-soluble and stable GMC1 formulation.

Formula I (GMC1)

In certain aspects GMC1 or an analog thereof is provided as a co-solvent formulation comprising of 20, 25, 30, 35, 40, 45, 50 to 40, 45, 50, 55, 60% Labrasol® (including all values and ranges there between), and 20, 25, 30, 35, 40, 45, 50 to 40, 45, 50, 55, 60% PEG 300 (including all values and ranges there between) containing 1, 10, 25, 50, 75 to 50, 75, 100, 125, 200 mg/mL of GMC1 (including all values and ranges there between). In certain aspects the co-solvent formulation comprises 50% Labrasol® and 50% PEG 300 containing 10 mg/mL of GMC1.

Certain embodiments are directed to a sensitive and reliable LC/MS/MS analytical method for the quantification of GMC1 during pre-formulation and formulation studies, pharmacokinetic studies, and other future preclinical and clinical studies involving GMC1.

Certain aspects are directed to a method for assessing GMC1 in a sample comprising: (a) separating GMC1 containing sample using liquid chromatography (LC) over a C18 column with a binary solvent system, the solvent system comprising a first solvent of 0.1% formic acid in water and a second solvent of 0.1% formic acid in methanol; (b) collecting LC fractions for analysis by mass spectrometry; (c) introducing collected fraction(s) into a mass spectrometer for multiple reaction monitoring (MRM) detection of ions produced from GMC1 in the collected fractions; and (d) detecting ions produced from ionization of GMC1. In certain aspects the m/z 341.05 to m/z 191.0 transition is indicative of GMC1. The GMC1 containing sample can be a methanol or acetonitrile extract of a biological sample. The biological sample can be a biological fluid or tissue homogenate. In a further aspect the biological sample is blood or urine. In certain embodiments the biological sample can be processed by extraction, precipitation, etc. prior to evaluation.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIGS. 1A-1B. The product ion mass spectra.

FIGS. 2A-2B.

FIGS. 4A-4C. Log of plasma concentration of GMC1 (in ng/mL) after a 2 mg/kg single IV bolus dose of the optimal co-solvent formulation in Sprague Dawley rats plotted against time.

DESCRIPTION

Androgen and androgen receptor (AR) signals are required for prostate development, differentiation, normal functioning, as well as cancer initiation and progression (Yeh, et al., *Differential roles of androgen receptor. Androgen Action in Prostate Cancer*, ed. Tindall and Mohler. 2009: Springer Science+Business Media). Current prostate cancer therapies antagonize androgen by competing for the androgen receptor (AR) binding pocket. However, this treatment option becomes essentially ineffective once androgen-dependence is lost (Heinlein and Chang, *Endocrine Reviews*, 2004, 25(2):276-308). The 52 kDa FK506 binding protein (FKBP52), a known positive regulator of androgen (AR), glucocorticoid (GR), and progesterone receptor (PR) function, and the developmental regulator β-catenin, represent potential therapeutic targets for the treatment of prostate cancer (Storer Samaniego et al., *PLoS One*, 2015, 10(7): e0134015).

GMC1 has been identified and characterized as a direct FKBP52 inhibitor, effectively inhibiting androgen receptor (AR) and glucocorticoid receptor (GR) activity in a variety of cell lines. This molecule effectively inhibits receptor activity in the low to mid micro-molar concentrations, causing reduced AR protein levels in the cytoplasm. This suggests increased AR degradation, leading to the inhibition of AR-dependent prostate-specific antigen (PSA) secretion from a variety of prostate cancer cells (De Leon et al., *Proc Natl Acad Sci USA*, 2011, 108(29):11878-834). In addition, GMC1 effectively inhibits 22Rv1 prostate cancer cell proliferation in the low micromolar concentration range.

GMC1 is a first-in-class drug for the direct targeting of an androgen receptor-associated co-chaperone for the treatment of castration-resistant prostate cancer (CRPC). It is desirable for the preclinical development of the poorly water soluble GMC1 to have a suitable water soluble and stable liquid dosage form suitable for intravenous administration. The inventors have developed a co-solvent formulation of GMC1 which has increased the water solubility of GMC by over 3,500 fold. In addition the inventors have also developed and validated a sensitive and reliable LC/MS/MS method for the analysis of GMC1 in solution, plasma, and urine.

I. Methods for Treating

Certain embodiments are directed to methods of treating hormone receptor associated conditions, such as those associated with androgen receptor, glucocorticoid receptor, and/or progesterone receptor. Certain aspects are directed to treating cancers associated with AR activity. In a further aspect a subject with prostate or breast cancer can be administered the compositions described herein.

Prostate cancer is a proliferative disorder characterized by abnormal cell growth that originates in the prostate gland. A proliferative disorder refers to any cellular disorder in which the cells proliferate more rapidly than normal tissue growth. A proliferative disorder includes, but is not limited to, neoplasms, which are also referred to as tumors. Prostate cancer tumors can be adenocarcinomas of epithelial origin. Prostate cancer tumors can comprise prostate luminal epithelial cells, prostate basal epithelial cells, stromal cells, or a combination of prostate luminal epithelial, prostate basal epithelial cells, or stromal cells. Prostate cancer tumors can comprise CK8+ prostate luminal epithelial cells. Prostate cancer tumors can also comprise CK5+ prostate basal epithelial cells which are also known as stem/progenitor/basal epithelial cells.

Breast cancer is a disease that kills over 45,000 women each year in the United States alone. Over 180,000 new cases of breast cancer are diagnosed annually, and it is estimated that one in eight women will develop breast cancer. These numbers indicate that breast cancer is one of the most dangerous diseases facing women today. The standard of care currently includes screening the tumor for the expression levels of the hormone receptors, estrogen receptor (ER) and progesterone receptor (PR), and the human epidermal growth factor receptor 2 (HER2) kinase. Hormone receptor positive breast cancers are susceptible to hormone therapies with selective estrogen receptor modulators or SERMs (e.g., tamoxifen, toremifene), aromatase inhibitors (e.g., anastrozole), or selective estrogen receptor degraders or SERDs (e.g., fulvestrant). Despite multiple tiers of targeted treatments, patients often have or develop refractory forms of breast cancer. Examples of refractory breast cancer include primary tumors which are triple-negative (lacking ER, PR, HER2), hormone resistant (SERM-, SERD-, or AI-resistant), or kinase inhibitor resistant, or metastatic breast cancer tumors.

As used herein, treating cancer includes preventing, precluding, delaying, averting, obviating, forestalling, stopping, or hindering the onset, incidence, or severity of the cancer or the recurrence of the cancer in a subject. In certain aspects the cancer is prostate or breast cancer. As utilized herein, by recurrence of cancer is meant the reappearance of one or more clinical symptoms of cancer after a period devoid of one or more clinical symptoms of cancer. The disclosed method is considered to reduce the occurrence or recurrence of cancer if there is a reduction or delay in onset, incidence, or severity of the reappearance of cancer, or one or more symptoms of cancer (e.g., with prostate cancer—problems urinating, pain during urination, pelvic discomfort, swelling in the legs as a result of edema, blood in urine, swelling of the lymph glands, bone pain) in a subject at risk for occurrence or recurrence of cancer.

Described herein are methods and formulations for treating or reducing the recurrence of hormone receptor dependent conditions, such as prostate cancer. Certain embodiments are directed to methods of treating the occurrence or reducing the likelihood of recurrence of prostate cancer in a subject, comprising administering to the subject an effective amount of the GMC1 formulations described herein. In a further aspect, the methods include administering to the subject an effective amount of a formulation described herein, wherein the subject is identified as having or is at risk for occurrence or recurrence of prostate cancer.

As used throughout, subject means an individual. Preferably, the subject is a mammal and, more preferably, a human. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Veterinary uses and formulations for the same are also contemplated herein. As utilized herein, a subject at risk for recurrence of prostate cancer is a subject that is at risk for the reappearance of prostate cancer after treatment for prostate cancer or after remission from prostate cancer.

Standard treatment methods or therapies for prostate cancer include, but are not limited to, orchiectomy (surgical castration), prostatectomy, anti-androgen therapy (for example, Eulexin®, Casodex®, Nilandron® and Nizoral®), radiation therapy, chemotherapy, luteinizing hormone releasing hormone analogs (for example, Lupron®, Viadur®, Eligard®, Zoladex®, Trelstar® and Vantas®), luteinizing hormone releasing hormone antagonists (for example, Plenaxis® and Firmagon®) or combinations of these treatment methods. After treatment, a subject can be monitored for recurrence of prostate cancer. Routine follow up visits after treatment allow one of skill in the art to determine if the subject is devoid of clinical symptoms or if clinical symptoms of prostate cancer have reappeared. In order to determine the status of the subject, a blood test to measure PSA levels can be performed. The results of the PSA test can indicate that prostate cancer can or has recurred. Imaging techniques, such as X-rays, MRIs, CT scans and bone scans can also be used. Lymph node examinations, biopsies, and digital rectal examinations can also be utilized to identify a subject at risk for occurrence or recurrence of prostate cancer. These techniques can also be used to stage any occurrence or recurrence of prostate cancer.

Also provided is a method of treating prostate cancer in a subject, comprising selecting a subject with prostate cancer and administering to the subject an effective amount of a formulation described herein.

Further provided is a method of reducing prostate tumor progression in a subject, comprising administering to the subject an effective amount of a formulation described herein. This method can be performed in combination with anti-androgen therapy that decreases proliferation of prostate cancer cells. In certain aspects the prostate cancer cells are luminal epithelial cells and/or stromal cells. In other aspects the formulation can be administered independently of anti-androgen therapy.

As utilized herein, by reducing prostate tumor progression is meant a method of preventing, precluding, or hindering prostate tumor progression in a subject. The disclosed method is considered to reduce prostate tumor progression if there is a reduction or delay in prostate tumor growth, metastasis, or one or more symptoms of prostate cancer (e.g., problems urinating, pain during urination, pelvic discomfort, swelling in the legs as a result of edema, blood in urine, swelling of the lymph glands, bone pain) in a subject with a prostate tumor.

In certain aspects a formulation described herein can be in a liquid or aqueous dosage form, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

Administration can be carried out using therapeutically effective amounts of the formulation described herein for periods of time effective to treat or reduce recurrence of prostate cancer or other hormone receptor associated conditions. The effective amount may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day.

According to the methods taught herein, the subject is administered an effective amount of the formulation. The terms effective amount and effective dosage are used interchangeably. The term effective amount is defined as any amount necessary to produce a desired physiologic response. Effective amounts and schedules for administering the formulations may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the activity of the specific compound employed, the metabolic stability and length of action of that compound, the species, age, body weight, general health, sex and diet of the subject, the mode and time of administration, rate of excretion, drug combination, and severity of the particular condition and can be determined by one of skill in the art. The dosage can be adjusted by the physician as needed, e.g., in the event of any contraindications. Dosages can vary, and can be administered in one or more dose administrations daily, for one or several days.

Any appropriate route of administration may be employed, for example, parenteral, intravenous, subcutaneous, intramuscular, intraventricular, intracorporeal, intraperitoneal, or oral administration. Administration can be systemic or local. Pharmaceutical compositions can be delivered intravenously. Multiple administrations and/or dosages can also be used. Effective doses can be extrapolated from dose-response curves derived from in vitro or animal model test systems.

The disclosure also provides a pharmaceutical pack or kit comprising one or more containers filled with one or more of the ingredients of the pharmaceutical compositions. Instructions for use of the composition can also be included.

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

LC/MS/MS Assay Method Development and Validation for Quantification of GMC1 in Solution, Plasma and Urine A simple, specific, sensitive and reliable LC/MS/MS method has been developed for the determination of the concentration of GMC1 in solution, plasma, and urine. This validated method is suitable for the determination of GMC1 in preclinical studies: preformulation, formulation, and pharmacokinetic studies as well as clinical studies. Analyst® Software 1.6 (AB Sciex, Foster City, Calif.) was used to control the LC/MS/MS system and analyze data. Chromatographic analysis was performed using 4000 QTRAP® LC/MS/MS system (AB Sciex, Foster City, Calif.), a hybrid triple quadrupole LIT (linear ion trap) mass spectrometer equipped with a Turbo V™ ion source. Pure nitrogen (curtain gas), source and exhaust gases were generated by a Peak Scientific GENIUS ABN2ZA Tri Gas Generator. The IonSpray heater was maintained at 700° C. with both the nebulizer gas and heater gas set to 50 and 30 psi respectively. The IonSpray voltage was set to 1100 V; the curtain gas set to 25 psi and the collision CAD gas set to high. Multiple reaction monitoring (MRM) method in the positive mode was used to detect the transition ions from a specific precursor ion to the product ion for GMC1 ($[M+H]^+$ m/z 341.05→m/z 191.0) and the internal standard ($[M+H]^+$ m/z 266.07→m/z 234.1). The collision energy was set at 27 eV for GMC1 and internal standard, respectively. Albendazole was used as an internal standard (IS).

Figure 1A:
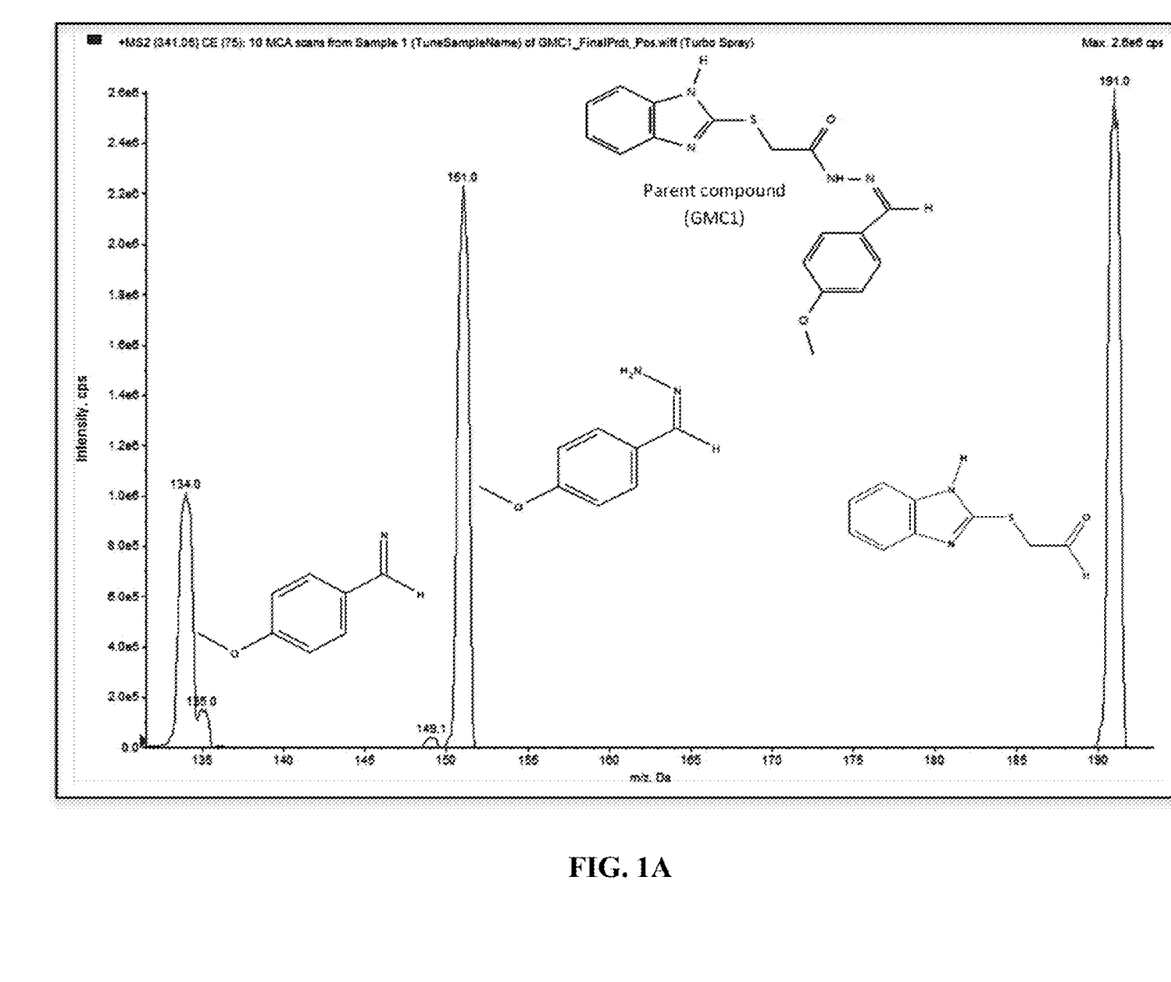
(FIG. 1A) GMC1 precursor ion to product ions (m/z 341→m/z 191) scan.
Figure 1B:
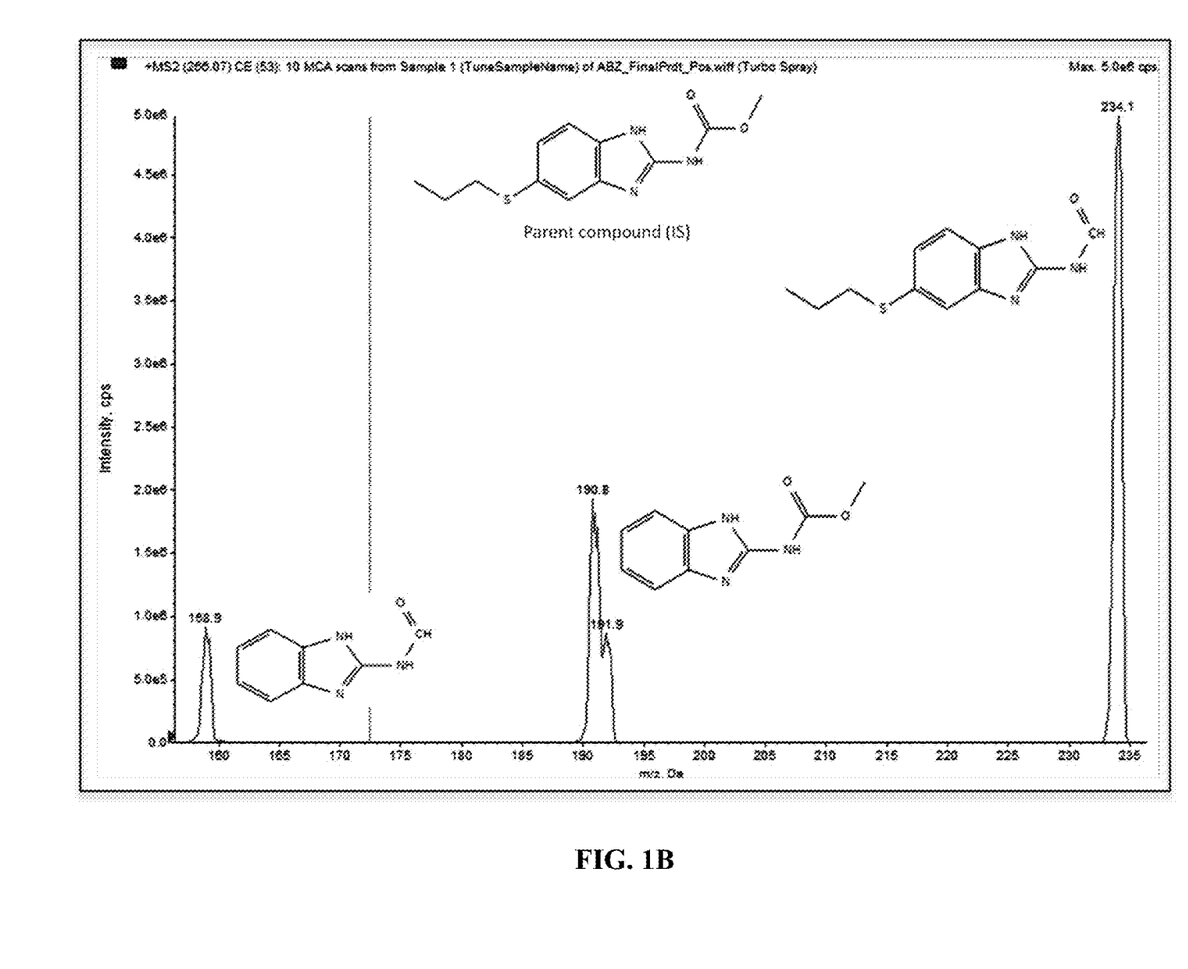
(FIG. 1B) Albendazole (IS) precursor ion to product ions (m/z 266→m/z 234).
Figure 2A:
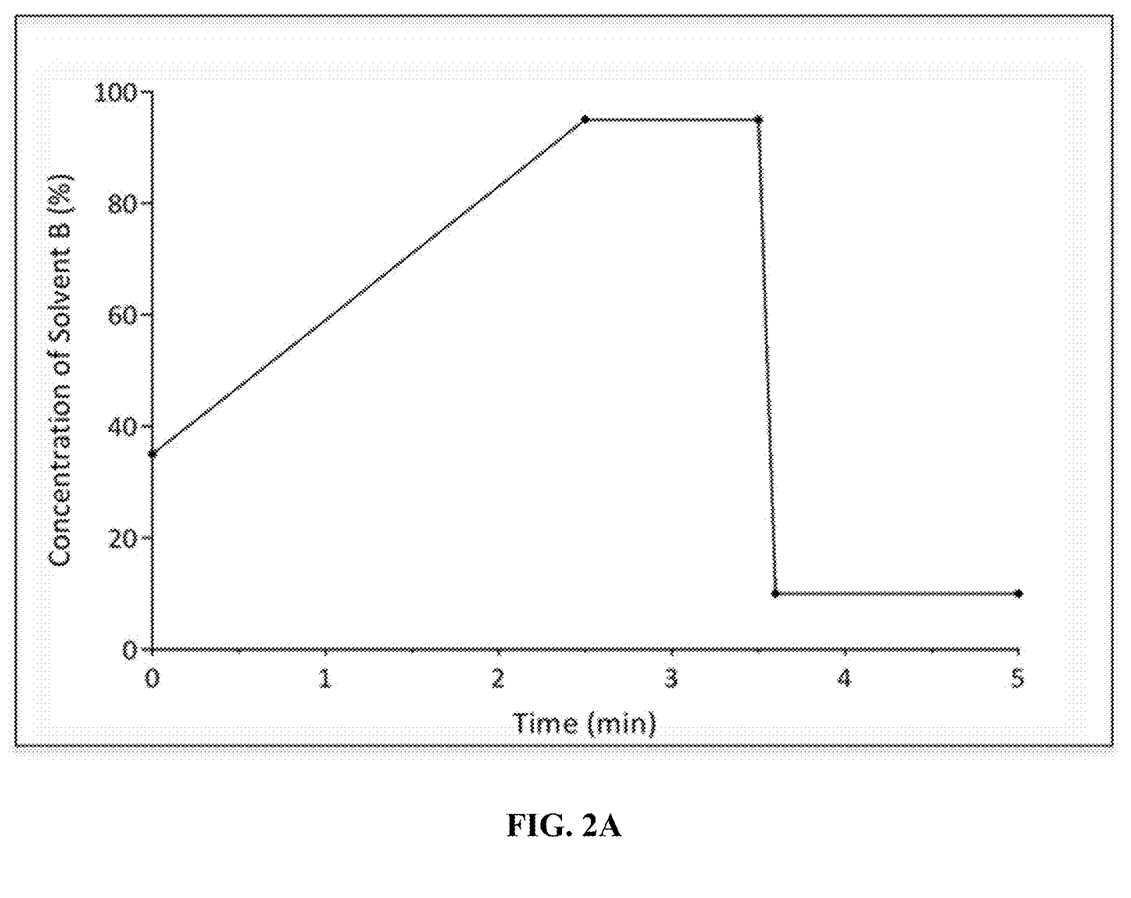
(FIG. 2A) Plot of the gradient elution showing changing concentration of solvent B with time.
Figure 2B:
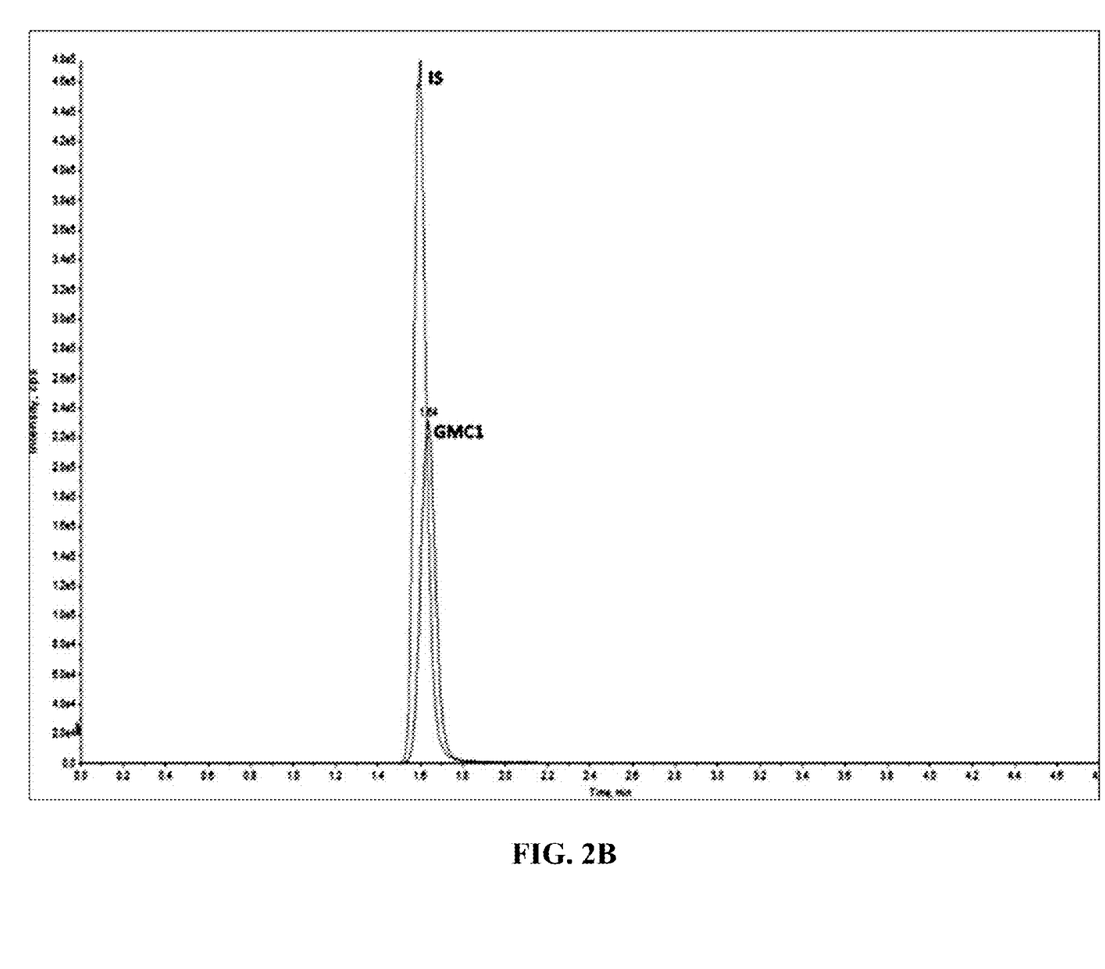
(FIG. 2B) Representative LC/MS/MS chromatograms of blank rat plasma spiked with GMC1 (250 ng/mL) and IS.

Chromatographic separation was achieved with a Waters XTerra® MS C18 column (3.5 μm, 4.6×50 mm, Milford, Mass.) using a Shimadzu Nexera X2 UHPLC System (Columbia, Md.). A binary solvent system was used: Solvent A was LC-MS grade water containing 0.1% formic acid and Solvent B was LC-MS grade methanol containing 0.1% formic acid. All samples were analyzed using gradient elution: initial 35% B, 95% B from 2.5-3.5 min, and 10% B from 3.6-5 min at a flow rate of 0.5 mL/min (FIG. 2A). An injection volume of 10 μL was employed. The retention times for GMC1 and IS were 1.78 and 1.64 respectively (FIG. 2B).

Working stock solutions of GMC1 and IS were prepared by dissolving in LCMS grade methanol at concentrations of 1 mg/mL and 0.5 mg/mL respectively. The stock solutions were stored at 4° C. until use. Standard samples of GMC1 were prepared in mobile phase (35% methanol in water) and rat plasma and urine at different concentrations: 1-500 ng/mL. Quality control (QC) samples of GMC1 were prepared in mobile phase and rat plasma and urine at low (10 ng/mL), medium (200 ng/mL) and high (400 ng/mL) concentrations. The plasma and urine samples were prepared by protein precipitation method. Briefly, a 50 μL aliquot of plasma or urine sample was extracted with 200 μL of methanol containing 25 ng/mL of internal standard followed by vortex mixing for 1 minute. This was then centrifuged at 14,000 rpm for 10 min, the supernatant transferred to the autosampler vial and 10 μL injected into the column for LC/MS/MS analysis.

Linear calibration curves in solution, plasma, and urine were generated by plotting the peak area ratio of GMC1 to IS against known standard concentrations of GMC1. The slope, intercept and correlation coefficient of linear regression equation were estimated using least square regression analysis. The calibration curves of GMC1 in solution, plasma, and urine were linear in the concentration range of 1-500 ng/mL with correlation coefficient greater than 0.998. The lower limit of quantification (LLOQ) was determined based on a signal-to-noise ratio of at least 5:1.

TABLE 1

Intra- and inter-day accuracy and precision of GMC1 LC/MS/MS analysis

|  | | Intra-day (n = 6) | | Inter-day (n = 6) | |
| --- | --- | --- | --- | --- | --- |
|  | Concentration (ng/mL) | Accuracy (RE*, %) | Precision (CV*, %) | Accuracy (RE, %) | Precision (CV, %) |
| Solution | 10 | 5.324494 | 1.375268 | 8.115983 | 3.963069 |
|  | 200 | 4.002777 | 7.374867 | 5.955424 | 4.731072 |
|  | 400 | 1.595337 | 7.839976 | 4.506949 | 3.84894 |
| Plasma | 10 | 10.10206 | 7.359196 | 6.487028 | 6.871065 |
|  | 200 | 10.43258 | 3.254755 | 8.377561 | 4.585042 |
|  | 400 | 4.362274 | 3.002798 | 3.85003 | 3.02377 |
| Urine | 10 | 11.68731 | 4.119532 | 8.845988 | 4.641901 |
|  | 200 | 7.844572 | 7.234533 | 7.730013 | 7.108789 |
|  | 400 | 2.075387 | 4.322673 | 3.531553 | 4.681988 |

LC/MS/MS Assay Validation. Analysis of six replicates of quality control (QC) samples of three different concentrations (low, medium and high) were performed using a calibration curve constructed on the same day to determine the intra-day accuracy and precision. The inter-day accuracy and precision were determined by analyzing six replicates of QC samples of three different concentrations using calibration curves constructed on three different days. The accuracy of the assay was obtained by calculating the percentage relative error from the theoretical GMC1 concentrations, while the assay precision was reflected by the percentage coefficient of variation.

The data obtained (Table 1) shows that the accuracy and precision were within the 15% acceptance range. The LC/MS/MS method for the analysis of GMC1 was validated to be accurate and precise for the measurement of solution, plasma, and urine with GMC1 concentration ranging from 1-500 ng/mL.

The extraction recovery and matrix effect were determined by analyzing GMC1 samples of three different concentrations: 10, 200, and 400 ng/mL. The extraction recovery of GMC1 was calculated as follows:

$$\% \text{ Recovery} = \frac{Response_{extracted\ sample}}{Response_{post\text{-}extracted\ spiked\ sample}} \times 100\%,$$

where $Response_{exacted\ sample}$ is the average area count for GMC1 sample, which has been through the extraction process, and $Response_{post\text{-}extracted\ spiked\ sample}$ the average area count for GMC1 sample spiked into extracted matrix after the extraction procedure. The average extraction recovery rate obtained by measuring triplicates of QC samples at low, medium, and high concentration levels of GMC1 in rat plasma were 96.1±4.8%, 96.1±2.1% and 96.9±5.7%, respectively and 98.9±1.9, 96.4±2.9%, 101.8±4.4% respectively in rat urine (Liang et al., *Am J Mod Chromatogr*, 2014, 1(1):1-115).

The effect of the biological matrix on GMC1 concentration was calculated as follows:

$$\text{Matrix effect (\%)} = \left( \frac{Response_{post\text{-}extraction\ spike\ sample} - Response_{neat\ sample}}{Response_{neat\ sample}} \right) \times 100,$$

where $Response_{post\text{-}extraction\ spike\ sample}$ is the average peak area count for a sample to which GMC1 was spiked into extracted matrix after the extraction procedure, and $Response_{neat\ sample}$ is the average peak area count for the same concentration of GMC1 prepared in a neat solution (methanol). A positive value indicates the enhancement of the sample signal, while a negative value indicates suppression of the sample signal (Matuszewski et al., *Analytical Chemistry*, 2003, 75(13):3019-30). Average matrix effects of −2.9%±2.2, −2.1%±1.4, −4.5%±1.2 were obtained for low, medium, and high QC samples respectively. The data suggest that there was no measurable matrix effect that interfering with the determination GMC1 in rat plasma using this LC/MS/MS method.

The short-term (bench-top) stability of GMC1 plasma and urine samples was evaluated by analyzing three sets each of GMC1 plasma and urine samples freshly prepared and placed on the bench-top for 2, 4, and 6 h, respectively. All the samples were compared with freshly prepared samples of the same concentration. Average recoveries of 97.4±8.89%, 88.9±2.63% and 80.1±5.71% were obtained from plasma placed on the benchtop for 2, 4, and 6 h respectively. Average recovery from urine were 94.2±4.66%, 93.9±0.76%, 93.7±1.23% after 2, 4, and 6 h on the benchtop respectively. This indicates that GMC1 is stable in plasma and urine samples placed on the bench-top for up to 6 hours (Liang et al., Biomed Chromatogr, 2013, 27(1):58-66).

The freeze-thaw cycle stability of GMC1 plasma and urine samples was evaluated by comparing QC plasma and urine samples exposed to three cycles of freeze (at −80° C.) and thaw (room temperature) to freshly prepared QC samples at the same concentration. Average recoveries from freeze-thawed plasma samples were 106±5.9%, 98.5±3.7% and 94.1±2.9% for GMC1 concentrations of 10, 200 and 400 ng/mL respectively. Average recovery from urine samples were 113±8.9%, 101±3.9%, and 86.6±7.5% for 10, 200 and 400 ng/mL GMC1 concentrations respectively. This indicates that GMC1 is stable in rat plasma and urine after three cycles of freeze and thaw (Liang et al., *Am J Mod Chromatogr*, 2014, 1(1):1-11).

The stability of processed samples (on-instrument or auto-sampler stability) was also evaluated by comparing freshly prepared plasma and urine QC samples to samples placed on the auto-sampler for 2, 4, and 6 h respectively. One set of the plasma and urine QC samples was extracted with methanol containing IS, and another set with pure methanol without IS.

The plasma samples extracted with methanol containing IS displayed 89.9±4.7%, 97.5±1.5% and 96.2±5.6% average recoveries for 2 h, 4 h, and 6 h samples respectively, while the plasma samples extracted with pure methanol displayed 94.7±7.9%, 99.7±4.5% and 98.4±6.2% recoveries, respectively. Also, the urine samples extracted with methanol containing IS displayed 96.4±2.8%, 98.5±1.1% and 97.1±4.8% average recoveries for 2 h, 4 h, and 6 h samples respectively, while the urine samples extracted with pure methanol displayed 96.1±2.4%, 89.7±8.8% and 95.2±2.2% recoveries, respectively. These data indicate that processed GMC1 plasma and urine samples are stable on the instrument for up to 6 hours, and the stability is independent on the presence of internal standard (Liang et al., *Am J Mod Chromatogr*, 2014, 1(1):1-11).

TABLE 2

Stability of GMC1 in Rat Plasma/Urine Samples for LC-MS/MS Analysis [n = 3; (mean ± SD)]

| | Biological Matrix | Time | Mean Recovery ± SD | |
|---|---|---|---|---|
| Short-term/ Long-term Stability | Plasma | 2 h | 97.4 ± 8.89 | |
| | | 4 h | 88.9 ± 2.63 | |
| | | 6 h | 80.1 ± 5.71 | |
| | Urine | 2 h | 94.2 ± 4.66 | |
| | | 4 h | 93.9 ± 0.76 | |
| | | 6 h | 93.7 ± 1.23 | |

| | | | Mean Recovery ± SD | |
|---|---|---|---|---|
| | | Time (hr) | No IS | With IS |
| Processed sample or Auto-sampler stability | Plasma | 2 | 94.7 ± 7.94 | 89.9 ± 4.74 |
| | | 4 | 99.7 ± 4.58 | 97.5 ± 1.48 |
| | | 6 | 98.4 ± 6.24 | 96.2 ± 5.57 |
| | Urine | 2 | 96.1 ± 2.37 | 96.4 ± 2.79 |
| | | 4 | 89.7 ± 8.81 | 98.5 ± 1.09 |
| | | 6 | 95.2 ± 2.16 | 97.1 ± 4.80 |

TABLE 2-continued

Stability of GMC1 in Rat Plasma/Urine Samples for LC-MS/MS Analysis [n = 3; (mean ± SD)]

|  |  | Nominal Concentration (ng/mL) | Mean Recovery ± SD |
|---|---|---|---|
| Freeze-thaw Cycle Stability | Plasma | 10 | 106 ± 5.9 |
|  |  | 200 | 98.5 ± 3.7 |
|  |  | 400 | 94.1 ± 2.9 |
|  | Urine | 10 | 113 ± 8.9 |
|  |  | 200 | 101 ± 3.9 |
|  |  | 400 | 86.6 ± 7.5 |

EXAMPLE 2

Pre-Formulation Studies and Development of Intravenous Formulation

Solubility information in various solvents is important in developing a suitable intravenous formulation of GMC1 for preclinical and clinical studies. The solubility of GMC1 in water, ethanol, polyethylene glycol 300 and 400, propylene glycol monocapryrate type I (Capyrol 90®), dimethyl sulfoxide (DMSO), dimethyl acetamide (DMA), Tween 80®, Labrasol®, Labrafac®, soybean oil, and oleic acid were determined by the shaker method. Briefly, excess amount of GMC1 was added to each of the selected solvents in a scintillation vial and shook using a reciprocating shaker at room temperature for 72 h. The samples were centrifuged at 14,000 rpm for 10 min and subsequently filtered through a 0.22 μm filtration unit, the resulting filtrate analyzed by LC/MS/MS to determine the GMC1 dissolved in the solvents. The study was conducted in triplicate. The result, summarized in Table 3, revealed that GMC1 is poorly soluble in water (0.003 mg/mL), but very soluble in DMSO and DMA (≥100 mg/mL).

TABLE 3

Solubility of GMC1 in selected solvents.

| Solvent | Mean Solubility (mg/mL) ± SD |
|---|---|
| Labrasol | 36.4 ± 2.90 |
| Tween 80 | 20.3 ± 5.39 |
| PEG 400 | 35.7 ± 1.41 |
| PEG 300 | 36.6 ± 1.12 |
| D.I water | 0.4 ± 0.01 |
| Ethanol | 6.3 ± 0.29 |
| Soy bean oil | 1.1 ± 0.02 |
| Oleic Acid | 2.2 ± 0.02 |
| Labrafac | 1.2 ± 0.01 |
| DMSO | >100 |
| Dimethyl acetamide | >100 |

The water-octanol partition co-efficient (log P) of GMC1, a measure of how hydrophilic ("water-loving") or hydrophobic ("water-fearing") GMC1 is, was also evaluated using the shaker method. GMC1 was found to have a log P value of 3.48±0.03 indicating good solubility of a potential oral drug.

The poor water solubility of GMC1 can be improved by incorporating a water miscible solvent in which the molecule has a good solubility. This method, often called a co-solvent system, is a suitable means for formulating non-water-soluble drugs for intravenous administration. A co-solvent system suitable for intravenous administration must resist precipitation of the drug upon dilution with intravenous fluids or blood. Different co-solvent systems with varying compositions and ratio of solvents were prepared with GMC1 concentrations ranging from 5-20 mg/mL. Each system was diluted with normal saline (0.9% sodium chloride) at ratios of 1:2, 1:5, 1:10, 1:20 (v/v), to evaluate GMC1 precipitation within 6 hours.

Upon observation for 6 hours, absence of precipitation indicated that the formulation had a good capacity to keep GMC1 dissolved in an aqueous environment. It also indicated that an intravenous dose of this formulation would likely not cause precipitation at the site of injection. The optimal formulation was selected based on (1) solubility of GMC1, (2) precipitation of GMC1 upon dilution, (3) toxicity of the solvent, and (4) formulation stability. The various co-solvent systems formulated and their behaviors upon dilution with normal saline are summarized in Table 4.

TABLE 4

GMC1 co-solvent systems showing composition, ratio of components and precipitation upon dilution with normal saline at different ratios.

| | Composition and ratio of solvent (% v/v) | | | GMC1 | Precipitation upon dilution with normal saline (v/v) | | | |
|---|---|---|---|---|---|---|---|---|
| Label | Labrasol | PEG 300 | PEG 400 | Conc. (mg/mL) | 1:2 | 1:5 | 1:10 | 1:20 |
| L1 | 100 | | | 5 | Y | Y | Y | Y |
| P1 | | 100 | | 5 | Y | Y | Y | Y |
| P2 | | | 100 | 5 | Y | Y | Y | Y |
| PL1 | 30 | | 70 | 5 | N | N | N | N |
| PL1 | 70 | | 30 | 5 | N | N | N | N |
| PL3 | 50 | | 50 | 5 | N | N | N | N |
| LP1 | 30 | 70 | | 5 | N | N | N | N |
| LP2 | 70 | 30 | | 5 | N | N | N | N |
| LP3 | 50 | 50 | | 5 | N | N | N | N |
| PL4 | 30 | | 70 | 7.5 | N | Y | Y | Y |
| PL5 | 70 | | 30 | 7.5 | N | N | Y | Y |
| PL6 | 50 | | 50 | 7.5 | N | N | Y | Y |
| LP4 | 30 | 70 | | 7.5 | N | N | N | N |
| LP5 | 70 | 30 | | 7.5 | N | N | N | N |
| LP6 | 50 | 50 | | 7.5 | N | N | N | N |
| LP7 | 30 | 70 | | 10 | N | N | N | N |
| LP8 | 70 | 30 | | 10 | N | N | N | N |
| *LP9 | 50 | 50 | | 10 | N | N | N | N |
| LP10 | 30 | 70 | | 15 | Y | Y | Y | Y |
| LP11 | 70 | 30 | | 15 | Y | Y | Y | Y |
| LP12 | 50 | 50 | | 15 | Y | Y | Y | Y |

"Y" means precipitation and
"N" means no precipitation.
*LP9 comprising of 50% Labrasol® and 50% PEG 300 was selected as optimal formulation based on stability upon dilution with normal saline, and minimal toxicity of excipients.

After considering the factors listed above, the co-solvent systems comprising or consisting of 50% PEG 300 and 50% Labrasol® and 10 mg/mL GMC1 concentration was selected as the optimal co-solvent formulation. The formulation can be diluted with normal saline to the desired GMC1 concentration before IV bolus or infusion administration in preclinical and clinical settings.

The stability of the optimal co-solvent formulation at various storage temperatures was also investigated. Briefly, aliquots of the optimal co-solvent formulation of GMC1 were stored at different temperatures (−20° C., 4° C., and 25° C.) and analyzed using LC/MS/MS on Day 3, 7, 14 and 30 to determine the amount of GMC1 present.

TABLE 5

GMC1 optimal co-solvent formulation stability.

| | Storage condition | 3-days recovery (%) | 7-days recovery (%) | 14-days recovery (%) | 30-days recovery (%) |
|---|---|---|---|---|---|
| Optimal Co-solvent Formulation | −20° C. | 97.3 ± 3.5 | 93.7 ± 2.42 | 94.8 ± 0.1 | 95.9 ± 1.9 |
| | 4° C. | 100.8 ± 3.5 | 99.8 ± 0 | 98.9 ± 5.1 | 95.9 ± 5.8 |
| | 25° C. | 98.2 ± 3.9 | 86.3 ± 1.04 | 97.9 ± 6.5 | 84.1 ± 2.5 |

The experiments were conducted in triplicate. The stability data shows that the GMC1 formulation was very stable for up to one month when stored at −20° C., 4° C. and 25° C. (Table 5).

In Vitro Plasma Precipitation Screening. An in vitro plasma precipitation screening was performed to evaluate the tonicity of the optimal cosolvent formulation with respect to plasma. Different dilutions of the optimal cosolvent formulation of GMC1 was spiked at various ratios to rat plasma placed in a water bath at 37° C. for 4 hours. Normal saline was used as a negative control. Precipitation of plasma protein was observed in all the mixtures except when the formulation was diluted 10 times in normal saline before spiking at a ratio of 1:10 in plasma. This suggest that the formulation should be diluted 10 times with normal saline prior to administration in animal or human studies/use.

TABLE 6

In vitro plasma precipitation screening of the cosolvent formulation of GMC1

| Cosolvent dilution with normal saline | Ratio of diluted cosolvent to rat plasma | | |
|---|---|---|---|
| | 1:1 | 1:4 | 1:9 |
| 1:2 | + | + | + |
| 1:5 | + | + | + |
| 1:10 | + | + | − |

+ means precipitation within 4 hours at 37° C.;
− means no precipitation

Figure 3:
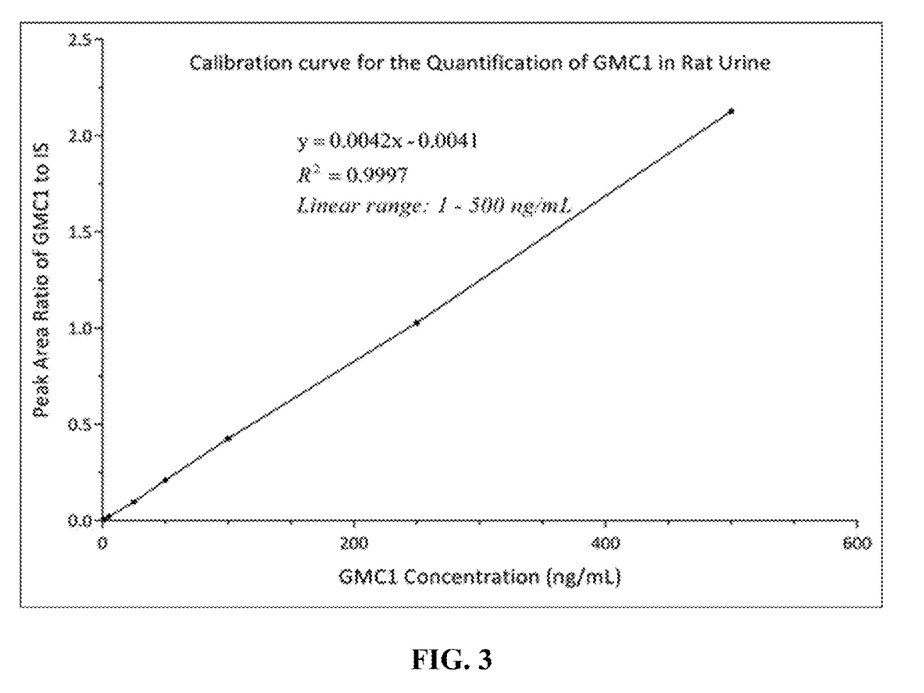
FIG. 3. Calibration curve for the quantification of GMC1 in rat urine.
Figure 4A:
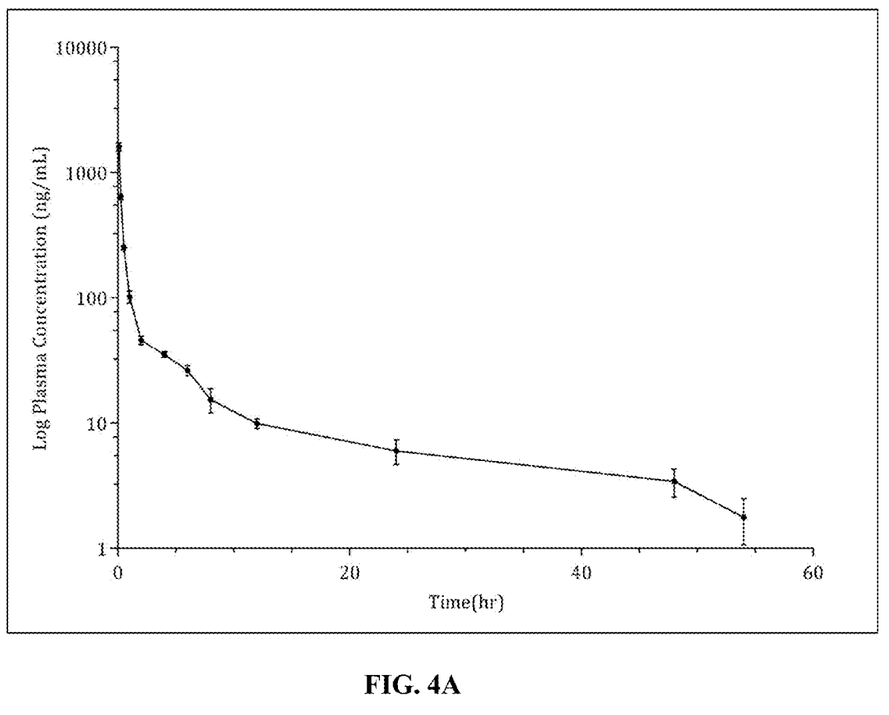
(FIG. 4A) Mean plasma concentration (n=4).
Figure 4B:
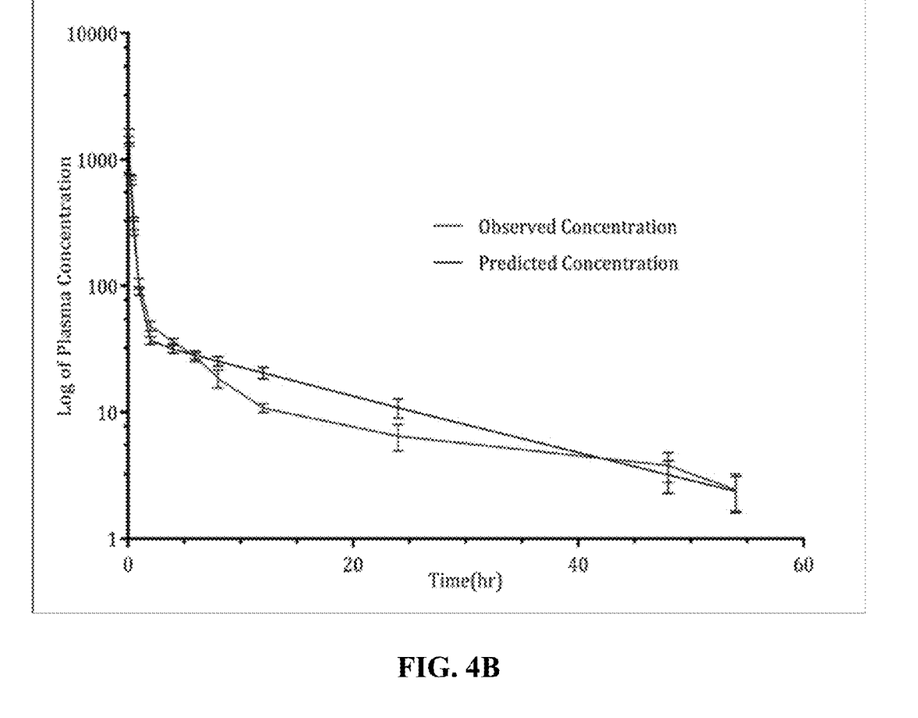
(FIG. 4B) Predicted versus observed plasma concentration of GMC1 (in ng/mL).
Figure 4C:
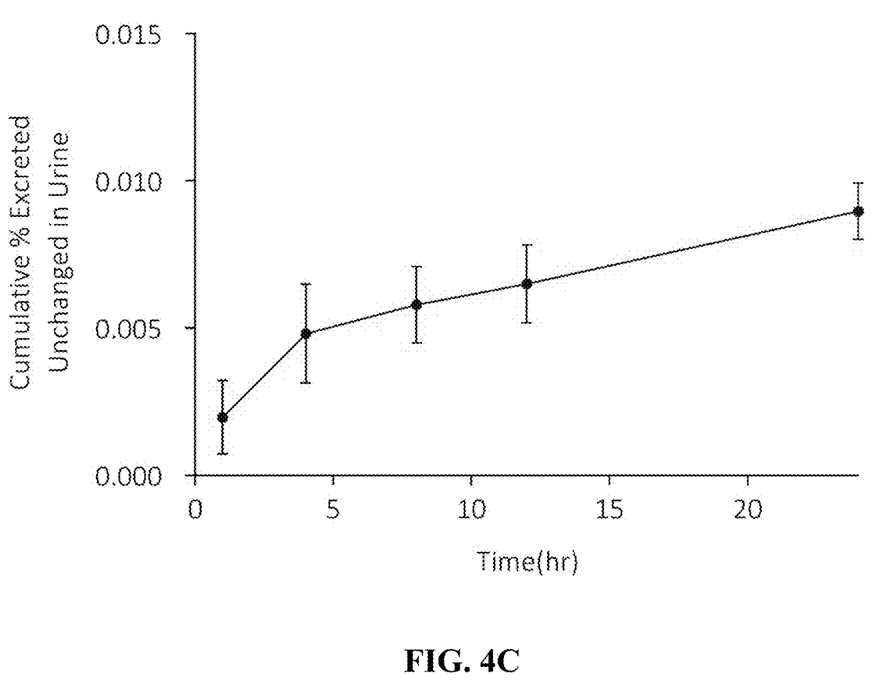
(FIG. 4C) Cumulative urinary excretion of GMC1.
Figure 5:
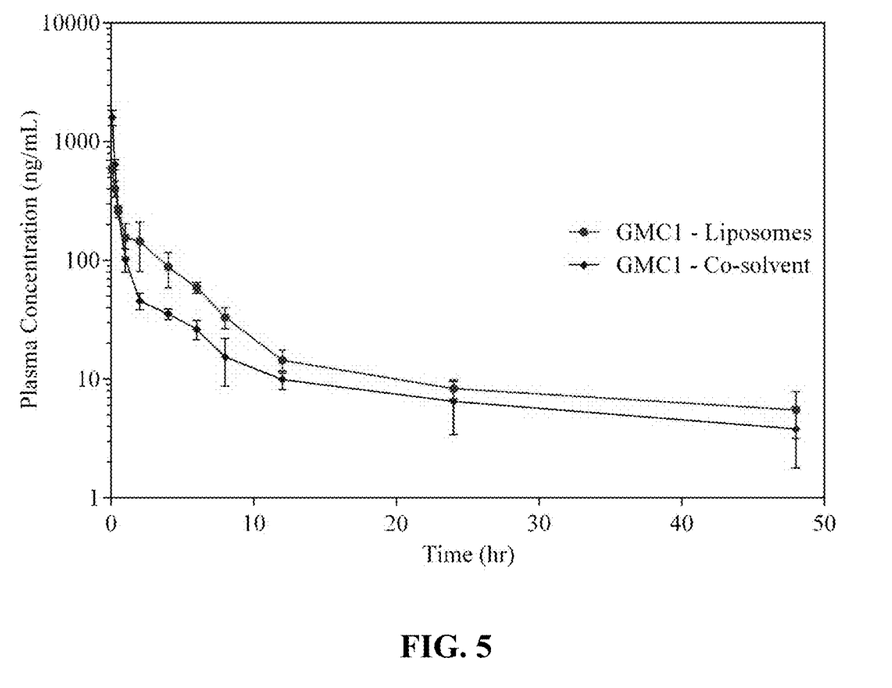
FIG. 5. Pharmacokinetic profile of GMC1 co-solvent and liposomal formulations.

Pharmacokinetic Studies of the GMC1 Co-Solvent Formulation. Pharmacokinetic study, which elucidates the fate of GMC1 in living systems, was performed. The pharmacokinetic study also verifies the applicability of the LC/MS/MS assay method and the formulation. A rat model was employed and male Sprague Dawley rats were selected as an animal model based on the similarity to humans in metabolism. Four male Sprague Dawley rats (body weight: 300-350 g) were cannulated through the jugular vein under anesthesia (using a cocktail of ketamine:acepromazine:xylazine at a ratio of 50:3.3:3.3 mg/kg). On the following day, the optimal co-solvent formulation of GMC1 (consisting of Labrasol® 50:50 PEG 300, and GMC1 10 mg/mL) was diluted ten times in normal saline to 1 mg/mL. Each rat was administered a 2 mg/kg IV bolus dose of GMC1. Heparinized blood samples were withdrawn from each rat at 5, 10, 15, 30, 60, 120, 240, 480, 720, 1440, 2880, 3240 min after injection. The blood samples were centrifuged at 14,000 rpm for 6 min and the supernatant plasma obtained and stored at −80° C. until analysis. Urine samples were also collected at 0, 60, 240, 480, 720, and 1440 min. The plasma and urine samples were analyzed (within 7 days) using the LC/MS/MS method described herein to obtain the concentration of GMC1. FIG. 3 shows a plot of the plasma concentration of GMC1 against time.

The pharmacokinetic parameters for each rat were determined with Phoenix WinNonlin 6.3 software (Pharsight Corporation, Mountain View, Calif., USA) using a three compartment, which best described the fit for the IV bolus administration of GMC1, based on the observed and predicted fits of the plasma concentration versus time plot, the reduction in the sums of squares, and the Akaike's information criterion (AIC) for comparing compartmental models (Yamaoka et al., *Journal of Pharmacokinetics and Biopharmaceutics* 1978, 6(2):165-75). The three-compartment model is described by the equation:

$$C_t = A \cdot e^{-\alpha t} + B \cdot e^{-\beta t} + C \cdot e^{-\gamma t}$$

where A, B and C are the coefficients, $\alpha$, $\beta$, and $\gamma$ are alpha, beta and gamma phase rate constants respectively, and $C_t$ is the plasma concentration of GMC1 at time, t.

TABLE 7

Pharmacokinetic parameters of GMC1 after administration of single 2 mg/kg IV bolus dose to rats (n = 4).

| Pharmacokinetic Property | Mean ± S.D |
|---|---|
| Cmax (ng/mL) | 7642.5 ± 1977.11 |
| A (ng/mL) | 6528.9 ± 1996.01 |
| $T_{1/2\alpha}$ (min) | 6.6 ± 2.16 |
| B (ng/mL) | 1038.5 ± 546.09 |
| $T_{1/2\beta}$ (min) | 73.8 ± 25.17 |
| C (ng/mL) | 75.1 ± 20.24 |
| $T_{1/2\gamma}$ (min) | 1179.6 ± 305.25 |
| $AUC_{0-\infty}$ (min · ng/mL) | 233735.8 ± 43938.11 |
| Cl (mL/kg/min) | 8.9 ± 1.66 |
| V1 (mL/kg) | 278.0 ± 64.20 |
| V2 (mL/kg) | 559.5 ± 206.03 |
| V3 (mL/kg) | 6866.5 ± 1117.54 |
| Vss (mL/kg) | 7726.5 ± 1222.34 |

$C_{max}$ = maximum concentration; A = coefficients of $\alpha$-phase; $T_{1/2\alpha}$ = distribution half-life of $\alpha$-phase; B = coefficients of $\beta$-phase; $T_{1/2\beta}$ = elimination half-life of $\beta$-phase; C = coefficients of $\gamma$-phase; $T_{1/2\gamma}$ = elimination half-life of $\gamma$-phase; $AUC_{0-\infty}$ = area under curve from time zero to infinity; Cl = total body clearance; $V_1$ = volume of distribution of central compartment; $V_2$ = volume of distribution of first peripheral compartment; $V_3$ = volume of distribution of second peripheral compartment; $V_{ss}$ = volume of distribution at steady state.

The weighting scheme of concentration$^{-2}$ ($Y^{-2}$) was used to determine the model that best fits the individual profiles. Table 5 shows the mean pharmacokinetic parameters. In summary, following the administration of 2 mg/kg IV bolus, an average maximum GMC1 plasma concentration (Cmax) of 7642.5±1977.11 ng/mL was reached, rapidly declining within the first hour, and steadily tailing off in the terminal elimination phase. The distribution phase half-life ($T_{1/2\alpha}$) was observed to be 6.6±2.16 min, the $\beta$-phase elimination half-life ($T_{1/2\beta}$) was 73.8±25.17 min, and the terminal elimination half-life was 1179.6±305.25 min.

Preparation of GMC1 Loaded Liposomes. GMC1-loaded liposomes were prepared by thin film hydration. The initial drug-to-lipid mole ratio was set at 1:6. DPPC and DSPC were selected as the phospholipids of choice; cholesterol was added for rigidity, while 5 moles % of DSPE-mPEG 2000 was added to PEGylate the liposomes for enhanced circulation and reduced clearance by the reticular endothelial systems. Several liposomal formulations with varying molar ratio of DPPC, DSPC and cholesterol were prepared and compared until the optimal formulation with acceptable particle size and encapsulation efficiency was obtained.

Briefly, appropriate amount of the GMC1, phospholipid(s), cholesterol and DSPE-mPEG 2000 were weighed and dissolve in a blend of chloroform and methanol mixed at a ratio of 2:1 (v/v). The organic solvents were evaporated in a rotatory evaporator with temperature set to 80° C. and vacuum pressure 400 psi. To form a suspension of multilamellar vesicles (MLVs), the resulting lipid film was hydrated with ultrapure water (temperature 60° C.) with gently continuous swirling in a water bath for up to 30 mins. The particle size of the MLVs were reduced by sonication at 10% amplitude for 10 mins using a Sonifier S-250D digital ultrasonic processor (Branson Ultrasonics Corporation, Danbury, Conn., USA). To ultimately reduce its particle size to within 100 nm, the liposome suspension was passed through 10 extrusion cycles using a Lipex extruder (Northern Lipids, Burnaby, BC, Canada) fitted with polycarbonate membrane filters with different sizes. Cycles 1-3 was performed with a membrane of pore size 1 μm, cycles 4-6 with 0.4 μm membrane and cycles 7-10 with membrane filter of pore size 0.1 μm.

Liposome Composition Optimization. The molar ratio of phospholipid (DPPC and/or DSPC) and cholesterol were varied until an optimal GMC1 loaded liposomes with desired characteristic was obtained. Liposomes with phospholipid:cholesterol:DSPE-mPEG 2000 molar ratio of 55:40:5 and 65:30:5 were evaluated. The phospholipid was either DPPC, DSPC or a blend of the two phospholipids at a ratio of 1:1, 3:1 or 1:3. The encapsulation efficiency and loading efficiency were calculated for each formulation; the optimal formulation was selected based on these.

Pharmacokinetic of GMC1-Loaded Liposomes. The pharmacokinetic profile of GMC1 encapsulated in PEGylated liposomes was also studied in a male SD rat model. The jugular vein of four adult male SD rats (average weight 0.326±0.007) were cannulated under anesthesia (ketamine: acepromazine: xylazine cocktail at a ratio of 50:3.3:3.3 mg/kg) one day prior to dosing. A single 1 mg/kg IV bolus dose of the liposomal formulation was administered to each rat. Blood samples of approximately 0.25 mL were withdrawn from each rat for up to 48 hours after the dosing. The blood samples were centrifuged at 13,000 rpm for 6 mins and the resultant supernatant (plasma) collected and stored at −80° C. until analysis. The plasma and urine samples were analyzed by LC-MS/MS for the concentration of GMC1. The pharmacokinetic parameters for GMC1 were estimated using Phoenix WinNonlin v7.0 software.

The pharmacokinetic parameters for GMC1 were computed using WinNonlin v7.0 via non-compartmental and compartmental analysis. Selection of the most suitable compartmental models for the pharmacokinetic analysis of the GMC1-loaded liposomes was also based on correlation coefficients, observed versus predicted plasma profile plots, Akaike inclusion criteria, Schwartz criteria and sums of square residuals or weighted sum of square residuals. Based on these criteria, a two-compartment model was selected for the compartmental analysis of the data.

The two-compartment model is described by the equation:

$$C_t = A \cdot e^{-\alpha t} + B \cdot e^{-\beta t}$$

where A, and B are coefficients, α, and β are alpha and beta phase rate constants respectively, and $C_t$ is the plasma concentration of GMC1 at time, t. Weighting factors of 1/Yhat*Yhat and 1/y*y were used for the compartmental and non-compartmental analysis of the data respectively.

Following the administration of a 1 mg/kg single IV bolus dose of the liposomal formulation, a maximum plasma concentration of 0.60±0.02 mg/L was reached, with a rapid distribution phase and slow elimination phase. An $AUC_{0-\infty}$ of 1.61±0.094 mg/L/hr was attained. The pharmacokinetic parameters obtained from the liposomal and co-solvent formulations were compared using a student t-test for the level of statistical significance between the two treatments. Parameters compared were the $C_{max}$, $Cl_T$, $V_D$, $V_{ss}$, $t_{1/2}$, and dose normalized $AUC_{0-\infty}$ obtained by non-compartmental analysis of the respective plasma concentration vs time profile. There was a statistically significant difference between the $C_{max}$, and $V_D$ estimated for the two formulations.

These data demonstrated that liposomal formulation of GMC1 significantly altered the intrinsic PK profile of GMC1. The bio-distribution of GMC1 following the administration of the co-solvent formulation depend largely on the nature of GMC1. Being lipophilic, it is extensively distributed to peripheral tissues, hence the third compartment in the model dependent analysis of the co-solvent—plasma concentration vs time profile. On the other hand, the PEGylated liposomal formulations increase the drug circulation in the central compartment, but decreases drug distribution to peripheral tissues. This protects the entrapped drug from metabolism and other mechanisms of degradation, thus enhancing the delivery of the drug to the tumor site by enhanced permeability and retention (EPR) effect.

Signs of hemolysis evident by the darkening of urine secreted by the rat were observed during the course of the PK study. A darkening of the urine was observed in the rats treated with the co-solvent formulation, but this was mitigated in the rats that received the liposomal formulation. The exact reason for the observation in the co-solvent treated rats is unknown—could be due to the drug or the excipients used. From a safety standpoint, it can be inferred that drug loaded liposomes is a safer formulation choice for the preclinical and subsequently clinical studies of GMC1.

TABLE 8

Comparison of the GMC1 PK parameters from both cosolvent and liposomal formulations. These PK parameters were generated by non-compartmental analysis.

| Pharmacokinetic Parameters (units) | Mean Estimate ± SD | | Statistical significance: P value |
|---|---|---|---|
| | Cosolvent formulation (n = 4) | Liposomal formulation (n = 4) | |
| $C_{max}$ (mg/L) | 4.66 ± 0.35 | 0.60 ± 0.02 | <0.001 |
| $T_{1/2}$ (hr) | 20.7 ± 3.74 | 30.5 ± 5.32 | NS |
| *$AUC_{0-\infty}$ (mg/L/hr) | 2.01 ± 0.19 | 1.61 ± 0.09 | NS |
| $Cl_T$ (L/kg/hr) | 0.51 ± 0.45 | 0.63 ± 0.04 | NS |
| $V_D$ (L/kg) | 14.5 ± 1.14 | 27.6 ± 4.70 | 0.03 |
| $V_{SS}$ (L/kg) | 7.57 ± 2.50 | 14.0 ± 3.15 | NS |

$C_{max}$ = maximum concentration; $T_{1/2}$ = elimination half-life; $AUC_{0-\infty}$ = area under curve from time zero to infinity; $Cl_T$ = total body clearance; $V_D$ = volume of distribution of central compartment;
*$AUC_{0-\infty}$ was dosed normalized by diving the $AUC_{0-\infty}$ by the dose of GMC1 administered.

Source of Materials. GMC1 was a gift from Dr. Marc B. Cox (El Paso, Tex.). Albendazole (purity≥98%), LC/MS grade water and methanol, formic acid, ethanol, Tween 80, olive oil, dimethyl sulfoxide, dimethyl acetamide, polyethylene glycol 300, polyethylene glycol 400 and 0.85% sodium chloride solution were purchased from Sigma Aldrich (St. Louis, Mo.). Labrasol® and Capyrol 90® were gifts from Gattefosse (Lyon, France). All chemicals and reagents were used as received. Freshly obtained human plasma was purchased from Gulf Coast Blood Center (Houston, Tex.) and fresh rat plasma and urine was collected from male Sprague-Dawley rats (Harlan Laboratories, Houston, Tex.) and stored at −80° C. until use.

The invention claimed is:

1. A co-solvent formulation comprising (i) 20 to 80% PEG 300, (ii) 20 to 80% caprylocaproyl polyoxyl-8 glycerides and (iii) 1 to 200 mg/mL GMC1, wherein GMC1 has a formula of:

2. The co-solvent formulation of claim 1, wherein the formulation comprises (i) 50% PEG 300, (ii) 50% caprylocaproyl polyoxyl-8 glycerides and (iii) 10 mg/mL GMC1.

3. A method of treating prostate cancer comprising administering to a subject having prostate cancer a formulation comprising (i) 20% to 80% PEG 300, (ii) 20% to 80% caprylocaproyl polyoxyl-8 glycerides and (iii) 1 to 200 mg/mL GMC1, wherein GMC1 has a formula of:

4. The method of claim 3, further comprising administering chemotherapy or radiation treatments.

\* \* \* \* \*

UNITED STATES PATENT AND TRADEMARK OFFICE
CERTIFICATE OF CORRECTION

PATENT NO. : 10,010,534 B2
APPLICATION NO. : 15/471102
DATED : July 3, 2018
INVENTOR(S) : Marc Cox, Huan Xie and Oscar Ekpenyong Page 1 of 1

It is certified that error appears in the above-identified patent and that said Letters Patent is hereby corrected as shown below:

In the Specification

Please replace Column 1, Lines 13-17 with the following:
This invention was made with government support under GM084863 awarded by the National Institutes of Health. The government has certain rights in the invention.

Signed and Sealed this
Fourteenth Day of January, 2025

Derrick Brent
*Acting Director of the United States Patent and Trademark Office*